United States Patent [19]
Reich

[11] Patent Number: 5,350,783
[45] Date of Patent: Sep. 27, 1994

[54] COMPOSTABLE THERMOPLASTIC PRODUCTS

[75] Inventor: Murray H. Reich, Princeton, N.J.

[73] Assignee: Biolan Corporation, Princeton, N.J.

[21] Appl. No.: 82,361

[22] Filed: Jun. 28, 1993

Related U.S. Application Data

[63] Continuation of Ser. No. 796,636, Nov. 21, 1991, abandoned.

[51] Int. Cl.$^5$ .................. C08K 3/00; C08K 5/56; C08K 5/09
[52] U.S. Cl. .................. 523/124; 523/125; 523/126; 523/128; 524/238; 524/239; 524/309; 524/314; 524/320; 524/322
[58] Field of Search ............... 523/124, 125, 126, 128; 524/309, 322, 314, 320, 238, 239

[56] References Cited
U.S. PATENT DOCUMENTS 3,856,889 12/1974 McConnell .................. 524/291
3,903,029 9/1975 Young .................. 524/222
3,921,333 11/1975 Clendinning et al. .................. 523/126

Primary Examiner—Paul R. Michl
Assistant Examiner—Olga Asinovsky
Attorney, Agent, or Firm—R. Gale Rhodes, Jr.

[57] ABSTRACT

Thermoplastic polymer product of a thermoplastic material including a thermoplastic polymer and polymeric composting promoting agent selected from the group consisting of nonmetallic metal complexing agents, nonoxidizing-metal metal complexing agents, and mixtures thereof, in a composting effective amount to convert in the presence of oxidizing metal compounds to an active oxidant to thermally degrade the thermoplastic polymer of the thermoplastic material under composting conditions to a low molecular weight material with enhanced biodegradability, the nonmetallic metal complexing agents and the nonoxidizing-metal metal complexing agents being neither photoactivators nor prooxidants.

19 Claims, No Drawings

COMPOSTABLE THERMOPLASTIC PRODUCTS

This is a continuation of application Ser. No. 07/796,636, filed Nov. 21, 1991 now abandoned.

The present invention refers to plastic structures such as agricultural films, liners for disposable diapers and sanitary napkins, trash bags, packaging films, plastic clips, plastic containers, and the like. Some plastic products are intended to be used indoors, or for relatively limited periods of outdoor exposure, after which the products are usually discarded. Examples of such plastic articles used indoors include packaging films for food, liners for disposable diapers, sanitary napkins, disposable clothing, cosmetic and pharmaceutical containers, containers for detergents and other cleaning agents, and many others. Examples of plastic articles exposed to the outdoors for limited periods of time include garbage bags, films used for construction purposes such as temporary windows and for curing concrete, agricultural mulch and fumigation films.

The explosive growth of plastics has aggravated the problem of disposing of solid waste materials and caused their accumulation in landfills, which accommodate over 90% of the country's solid waste at about 12,000 sites. Communities want to restrict the use of thermoplastics such as polyolefins and polystyrene since they do not biodegrade even under aerobic conditions, even though very little waste degrades in most landfills, because of anaerobic conditions. Responding to the shortage of landfills, municipalities have increased tipping charges.

To handle solid waste, several states have built facilities to compost sewage sludge and mixed solid wastes. However, thermoplastics do not degrade during composting into useful, nutrient-rich, soil-like material.

Thermoplastics have many different requirements. Polyolefin films are used as truck liners, garbage bags, liners for disposable diapers and sanitary napkins, agricultural mulch films, and packaging films. These films must be stable during relatively short exposures to sunlight. Truck liners are usually discarded without exposure to sunlight, and garbage bags require an outdoor stability of 30 to 60 days, in order to be sure that garbage does not spill out on the streets. They do not degrade at landfills and during composting of garden wastes.

The prior art does not teach the useful compostable thermoplastic polymer products taught herein. It is known that cellulose acetate, rice and corn starch have been claimed to make some thermoplastics such as polyethylene more susceptible to biodegradation. However, some question whether polyethylene has truly biodegraded. Also, starch decreases the strength of the films, and becomes unstable at temperatures above 230° C. (450° F.), which means that it is hard to blend into thermoplastic polymers such as polypropylene and polyamide which are extruded above 450° F.

U.S. Pat. No. 3,795,654 describes polyolefin films containing oxidizing metals and water soluble antioxidants such as lower alkyl thioureas, in amounts sufficient to stabilize the film, such that upon exposure to moisture that said water soluble antioxidants can be leached out in amounts sufficient to permit oxidative degradation. The oxidizing metals harm the physical properties of polyethylene film during processing as shown by a drop in the elongation from 393 and 514% for the control to as little as 176 and 413% for film made with 3% hydrated chromic oxide and 0.4% mixed metal oxides, and to 135% and 468% for film with 0.4% chromic oxide. Further the patent teaches that exposure of the film to water removes compounds from the film and does not teach that exposure to solutions of oxidizing metals converts metal complexing agents into active oxidants.

Several patents describe the use of metal complexes and organic salts of transition metals as prooxidants and photoactivators. Upon exposure to sunlight, the stabilizer is depleted and the photoactivator in the presence of sunlight accelerates the degradation of polyolefins, usually polyethylene. U.S. Pat. No. 4,519,161 teaches the use of an oxidizing metal such as an iron complex as the photoactivator. The complexing groups can be dithiocarbamate, dithiophosphate, xanthate, and cyclic phosphate.

A more recent patent application, U.S. Pat. No. 4,939,194, also teaches the combination of two metal complexes, not complexing agents. One complex is attached to the metal through oxygen and the metal is a transition metal, Fe, Mn, Ce, and the metal of the second metal complex is attached to the complexing agent through sulphur. Iron, manganese and cerium are oxidizing metals. The metal of the second metal complex is a transition metal or metal of group II or IV, of the period table, Co, Cu, Zn, and Ni. Further restriction of the invention is that the molar ratio of the second metal complex to the first metal complex is 0.5 or less. The purpose of this combination of metal complexes is to produce rapid photodegradation of the polymer after the stabilizing metal complex has been depleted by ultraviolet light. In this patent one oxidizing metal complex is a photoactivator and the other is a stabilizer. None of the above patents teach a compostable thermoplastic polymer product comprising a polymeric composting promoting agent selected from the group of metal complexing agents without metals and those which contain nonoxidizing metals, neither of which are photoactivators or prooxidants.

U.S. Pat. No. 4,983,651, teaches the use of a prooxidant, an antioxidant which is useful over a limited time, and an unsaturated polymer such as styrene/butadiene copolymer and natural rubber. The prooxidant is the organic salt of a transition metal, cobalt, manganese, and copper such as cobalt naphthenate. The metals are oxidizing metals. The notion taught by this invention is that the antioxidant will protect the polymer for a limited time in a composting urban garbage, after which the prooxidant in the presence of the unsaturated polymer will degrade the polymer. Of course, this limits the shelf life of the plastic product.

But the shelf life may be shortened by the excess thermal history of the product such as high processing temperatures and recycling of waste material in the plant. Both limitations are overcome by the present invention. Also, the patents do not describe a compostable thermoplastic polymer product comprising a polymeric composting promoting agent as described herein.

What this invention claims is a thermoplastic material including a thermoplastic polymer and polymeric composting promoting agent selected from the group consisting of nonmetallic metal complexing agents, nonoxidizing- metal metal complexing agents, and mixtures thereof in a composting effective amount to convert in the presence of oxidizing metal compounds to an active oxidant to thermally degrade said thermoplastic polymer of said thermoplastic material to a low molecular weight with enhanced biodegradability under composting conditions. Further, the polymeric composting promoting agent is neither a photoactivator nor a prooxidant.

This invention provides compostable thermoplastic polymers with commercial physical properties and shelf life.

By virtue of this invention, multi-layer and biaxially oriented packaging films, agricultural mulch, fumigation, and greenhouse films, disposable trash bags, chemical bags, liners for disposable diapers and sanitary napkins, truck liners, plastic containers and clips can be made from thermoplastics, which, depending upon the application, may be treated at facilities that handle sewage waste, food, leaves, and garden waste. After treatment, the thermoplastic polymer products are reduced to a low molecular weight material which will biodegrade to humus, carbon dioxide, and water. The final thermoplastic product can be used as a fertilizer for fields and golf courses, cover for landfill, and an additive for fertilizer.

It is an object of the present invention to provide compostable thermoplastic polymer products with commercial shelf life which may be treated at solid waste disposal facilities, as herein described, and/or discarded into sewage sludge, mixed solid waste, and garden waste composts so that the thermoplastic products are degraded to a low molecular weight material with enhanced biodegradability. The degraded thermoplastics will add to the total useful organic matter.

One object is to make compostable films for use as liners for disposable diapers and sanitary napkins. The films would have the required softness, flexibility, and strength, would retain liquids, urine and/or fecal matter, and after suitable treatment at a solid waste disposal facility would degrade by action of heat and bacteria.

Another object is to make compostable and degradable thermoplastic polymer films for use as bags for trash and chemicals. The film would retain all kinds of trash such as food, cans, paper, and chemicals for use in agriculture, and retain their strength in the sunlight. Then upon treatment herein taught, the films would degrade to a biodegradable material.

POLYMERS

The thermoplastic polymers of this invention include vinyl polymers and condensation polymers. Vinyl polymers include polyolefins, polyethylene, polypropylene, polybutene, polystyrene, polyvinyl chloride, polyvinyl acetate, polymethyl methacrylate, polyacrylonitrile, polystyrene, polymethylpentene, graft copolymers of polyolefins, acrylic polymers, copolymers of ethylene and acrylic acid, ethylene and vinyl alcohol, ethylene and ethylene acrylate, ethylene and methyl acrylate, ethylene and vinyl acetate, fluoroplastics, acrylonitrile copolymers, vinyl chloride copolymers, thermoplastic elastomers, terpolymers of ethylene, propylene and an nonconjugated diene, styrene/acrylonitrile copolymers, styrene and butadiene copolymers, styrene/maleic anhydride copolymers, polymers of ethylene, propylene, butene-1, and styrene, and co and terpolymers of ethylene, propylene, and butene with another olefin, with $C_6$-$C_{20}$ alpha olefins, styrene, and isoprene.

Thermoplastic polymers made by condensation methods include acetal polymers, polyamides, thermoplastic polyimides, cellulosics, polyethylene terephthalate, polyethersulfone, thermoplastic polyesters, aromatic polyesters, polycarbonates, polyarylsulfones, and polyurethanes. Preferred are polyolefins, more preferable are polymers of ethylene, propylene and butene, and most preferable are polypropylene, polybutene, copolymers propylene and ethylene and butene and ethylene and blends thereof.

ADDITIVES

It has been found that certain additives can be added which are polymeric composting promoting agents and which do not prematurely degrade the thermoplastic polymer during processing, indoor and outdoor storage, and use. In this invention, polymeric composting promoting agents include nonmetallic metal complexing agents, nonoxidizing-metal metal complexing agents, and mixtures thereof. Metal organic salts are included under metal complexing agents. The agents are neither photoactivators nor prooxidants.

The additives can be added as a polymer masterbatch. After suitable treatment of the discarded thermoplastic, the metal complexing material is converted to an active oxidant which thermally degrades the thermoplastic polymer product to a low molecular weight brittle material with enhanced biodegradability.

Polymeric composting promoting agents are selected from the group of metal complexing materials consisting of organic compounds such as beta-diketones, beta-ketoesters, phosphonic acids, aminopolycarboxylic acids, polyphosphates, hydroxycarboxylic and fatty acids, and materials containing —CO—, —$NH_2$, —SH, —S—S—, —COO—, and —$CO_2H$ groups. Aminocarboxylic acids include nitrilotriacetic acid, ethylenediaminetetraacetic acid, propylenediaminetetraacetic acid, diethylenetriaminetetraacetic acid, triethylenetetraaminetetraacetic acid, tetraethylenepentaaminetetraacetic acid. Some hydroxycarboxylic acids are gluconic, citric, tartaric, and saccharic acids, some fatty acids are stearic, lauric, myristic, oleic, naphthenic, octanoic, and linoleic acids and some beta-ketones are diones such as 2,4-pentanedione.

Other materials that will complex oxidizing metals are maleated polyolefins and polymers with carboxyl groups, such as propylene and acrylic acid copolymers, ethylene and acrylic acid copolymers with 1 to 30% acrylic acid, preferably 3 to 20%, ethylene and methacrylic acid copolymers, terpolymers of propylene, ethylene, and acrylic acid, and sodium and potassium salts of the acid polymers. Acid type polymers are added from 0.01 to 10%, preferably from 0.5 to 7% and more preferably from 1 to 5% based on the weight of the polymer product.

Maleated polyolefins include maleated polyethylenes and maleated polypropylene made by Eastman Kodak Company under the tradename of Epolene waxes. Epolene 43 has a molecular weight of 4500 and an acid number of 47. Other maleated polyolefins are maleated polypropylenes produced by DuPont under the tradename of Bynel 302, 304, and 379, and maleated polyethylene under Bynel 1000 to 4000 series. Maleated polymers are added from about 0.01% to 10%, preferably from 0.01% to 7%, more preferably from 0.1% to 5%, and most preferably from 0.2 to 3% by weight of said product.

Metal complexing agents include complexes of nonoxidizing metals such as aluminum, barium, calcium, magnesium, potassium, sodium, and titanium, preferably those of sodium, calcium, potassium, and magnesium. The metal complexes are neither prooxidants nor photoactivators and include sodium ethylenediaminetetraacetate, sodium salt of zinc ethylenediaminetetraacetate, calcium diethyldithiocarbamate, magnesium hydroxyethylethylenediaminetriacetic acid, sodium salt, calcium acetylacetonate, magnesium triethylenetetraaminetetraacetate, zinc diethylenetriamine pentaacetic acid, sodium salt, potassium propylenediaminetetraacetate, and nonoxidizing metal complexes of cyclic phosphate, xanthates, benzothiazoles, oximes, and benzimidazoles.

Polymeric composting promoting agent selected from the group of metal complexing agents which are not polymers may be added from 0.0005 to 5% by weight, preferably from 0.0005 to 3%, and more preferably from 0.0005 to 2%, and most preferably from 0.001 to 1%. The maximum ranges for metal complexing agents which are polymers is 10%, preferably 7%, more preferably 5%, and most preferably 3%.

Preferred materials for use in complexing metals are aminocarboxylic, hydroxycarboxylic, and fatty acids, beta-ketones, beta-ketoesters, dialklydithiocarbamates, polyphosphates, maleated polyolefins, and copolymers of ethylene and acrylic acid and methacrylic acid and their nonoxidizing metal salts and complexes especially those where the nonoxidizing and nonphotoactivating metal is attached to the metal complexing agent through an oxygen, and more especially acetylacetonates, stearates, octonates, and naphthenates. Combinations of metal complexing agents of nonoxidizing metals prepared from certain fatty acids, beta-ketoesters, and beta-ketones have been found to be especially useful, such as nonoxidizing metal salts of stearic, octanoic, and naphthenic acids and metal complexes of diones such as acetylacetone. Preferred nonoxidizing metals are calcium, magnesium, potassium, and sodium and preferred combinations of metal complexing agents and nonoxidizing metals include those comprising calcium, magnesium, potassium, and sodium octonates, napththenates, and acetylacetonates.

Processing oils such as naphthenic, paraffinic, and aromatic oils may be added with polymers of ethylene, butene, and propylene such as butene/ethylene, butene/propylene, and ethylene/propylene copolymers and ethylene/propylene/diene terpolymers, most preferably with terpolymers of ethylene, propylene, and a nonconjugated diolefin, and butene/ethylene copolymers, and may comprise 5 to 150 phr, preferably 20 to 125 phr, more preferably 30 to 110 phr of the modifier. Processing oils may comprise 0.05 to 20%, preferably from 0.1 i to 15%, more preferably from 1 to 10% by weight of thermoplastic polymer products. Processing oils enhance the thermal degradation of thermoplastics and the rate of biodegradation.

Preferred polymeric composting promoting agents are nonoxidizing metal organic salts and metal complexes of octanoic and naphthenic acids, and 2,4-pentanedione.

POST TREATMENT

This invention describes a process for forming a compostable thermoplastic material which comprises blending a thermoplastic polymer, a polymeric composting promoting agent selected from the groups consisting of nonmetallic metal complexing agents, nonoxidizing-metal metal complexing agents, and mixtures thereof, neither group being a photoactivator or prooxidant, said polymeric composting promoting agent being present in a composting effective amount to convert in the presence of oxidizing metal compounds to an active oxidant to thermally degrade the thermoplastic polymer of said thermoplastic material to a low molecular weight under composting conditions, said thermally degraded material having enhanced biodegradability.

Further herein described is a process for composting a thermoplastic material which comprises contacting said thermoplastic material with an effluent containing an oxidizing metal compound under composting conditions, said thermoplastic material comprised of a thermoplastic polymer and a polymeric composting promoting agent selected from the groups consisting of nonmetallic metal complexing agents, nonoxidizing-metal metal complexing agents, and mixtures thereof in a composting effective amount to convert in the presence of oxidizing metal compounds to an active oxidant to thermally degrade to a low molecular weight the thermoplastic polymer of said thermoplastic material under composting conditions, said thermally degraded material having enhanced biodegradability, and said metal complexing groups are neither a photoactivator nor a prooxidant.

In all processes, it has been surprisingly found that when thermoplastic polymer products containing a sufficient amount of a composting promoting agent are exposed to oxidizing metals in a media that active oxidants are formed which degrade the polymer to a low molecular weight material. The oxidizing metals include iron, copper, manganese, cobalt, cerium, silver, tungsten, cerium, chromium, nickel, palladium, molybdenum, vanadium, and zinc, preferably manganese, cobalt, copper, and iron. The oxidizing metals will displace nonoxidizing metals such as calcium, sodium, potassium, and magnesium. Some oxidizing metals, being higher on the metal displacement table than some nonoxidizing metals, displace the nonoxidizing metal in the complex and organic salt and are incorporated into the polymer product.

In one type of post treatment, discarded thermoplastic polymer products containing polymeric composting promoting agents selected from the group of metal complexing agents are delivered with other solid waste to a waste treatment facility. Ferrous and non-ferrous metals and glass containers are separated from the organic waste which is shredded and mixed with sewage sludge of pH 4 to 14, 10 to 40% solids, and containing oxidizing metals such as iron, copper, cobalt, and manganese. The mixture of sludge and organic waste is digested for about 3 to about 60 days at about 10° to about 80° C. to kill pathogens. The compost is cured for about 30 to about 90 days in aerated windrows, and in an open pile for about one to about six months to complete degradation of the organic waste. During this period metal complexing agents in the thermoplastic polymer product are converted to active oxidants which degrade the polymer to a low molecular weight biodegradable material. Garden and food waste also contain significant quantities of oxidizing metals and can be used to incorporate oxidizing metals into waste thermoplastic polymer products.

pH of the sewage sludge is about 4 to about 14, preferably 5 to 12, solids content of the sludge is about 2 to about 50%, preferably 4 to 30%, more preferably 10 to 25%, and digestion time is 3 to 72 days, preferably 5 to 28 days, and more preferably seven to 21 days.

Other treatments include immersion of discarded and shredded thermoplastic polymer products in solutions of oxidizing metals at about 0° to about 150° C. Then, the treated thermoplastic polymer products can be mixed with sewage sludge, garden waste, mixed solid organic waste, compost piles, and composted for about 3 days to about 6 months at temperatures from about 10° to about 80° C. Also, treated thermoplastic polymer products and sewage sludge can be dried at about 40° to about 150° C. for 1 minute to 24 hours to kill all bacteria and degrade the thermoplastic. Polymer waste from all treatments can be composted, cured, and mixed with fertilizer materials.

The tendency of the degraded thermoplastics with active oxidants to biodegrade can be determined by measuring the total amount of carbon dioxide which is evolved over a period of several months for samples placed in about 25 to 50 grams (dry weight) of fresh agricultural soil. Biometer flasks containing the soil are incubated at room temperature and 37° C. The control is polyethylene film which does not biodegrade in soil, even under very favorable conditions. Cumulative evolution of carbon dioxide is measured volumetrically over a period of several months, and $CO_2$ evolution curves are compared.

For this invention, 'compostable' is defined as material which is capable of being thermally degraded to a sufficiently low molecular weight under composting conditions, to enable the thermally degraded low molecular weight material to biodegrade at substantially higher rates than would nondegraded material of higher molecular weight. Included under the term composting conditions is the composting and curing of waste for one to eighteen months in aerated windrows, conveyor systems and open compost piles. During this period the organic waste continues to biodegrade, the thermoplastic polymer product thermally degrades, and the thermally degraded low molecular weight material at least partially biodegrades. Composting conditions also are defined as conditions which are favorable to biodegradation of the materials, such as exists when thermally degraded materials are mixed with fertilizer, used as a cover for landfills, farmland, and golf courses. A significant change in the rate of biodegradation is an increase from zero to about 1% or more of material within about three months under aerobic conditions.

In the stage prior to embrittlement, the thermoplastic product retains its integrity and properties during storage and usage. This means that films used as liners for disposable diapers retain the urine and feces during usage, liners for sanitary napkins retain liquids, truck liners keep the insides of trucks clean, greenhouse films remain intact, thermoplastic clips remain flexible, plastic containers are strong, fumigation films remain strong while they cover the field, and trash bags hold their contents until they are transferred to the waste treatment facility.

The thermoplastic polymer product breaks down over a period of three stages. During the initial stage, the polymer product comprising the polymeric composting promoting agent is exposed to oxidizing metals, and an active metal oxidant is formed by complexing and displacement mechanisms.

During the second stage, the oxidant accelerates the degradation of the thermoplastic polymer chains, and the polymer product loses its strength and elongation, becoming very brittle. Finally, the elongation drops to almost zero. The polymer product continues to degrade to a low molecular weight material with enhanced biodegradability. In the third stage the low molecular weight material biodegrades at temperatures of 10° to 100° C. and in the presence of bacteria, enzymes, and soil microorganisms to useful humus, carbon dioxide, and water.

In brief summary, it has been discovered in accordance with the teachings of the present invention that a thermoplastic polymer product containing a polymeric composting promoting agent selected from the group of nonmetallic metal complexing agents, and nonoxidizing-metal metal complexing agents, said agents being neither photoactivators or prooxidants, said metal complexing agent contained in an amount sufficient to promote compostability of the polymer product, such that upon exposure to oxidizing metals in a media said metal complexing agent is converted to an active oxidant in an amount sufficient, to thermally degrade the polymer product under composting conditions to a low molecular weight material having enhanced biodegradability. Media may be selected from the group of garden, lawn, organic, food, and mixed solids waste, lime, sewage sludge, manure, and solutions of oxidizing metals.

Further, this invention teaches a process for composting thermoplastic polymer products including the steps of providing a polymer product containing a metal complexing agent in an amount sufficient to promote compostability of the polymer product, exposing said polymer product to oxidizing metals to convert said complexing agent to an active oxidant in an amount sufficient to thermally degrade under composting conditions the polymer product to a low molecular weight material having enhanced biodegradability.

It is understood that the process of exposing thermoplastic polymer products to oxidizing metals also includes cases where the thermoplastic polymer comprises metal complexes of strong oxidizing metals such as ferric and cupric acetylacetonate where the metal complexing agent is attached to a strong oxidizing metal such as iron, manganese, cerium, and copper through oxygen and a stabilizing metal complexing agent where a weaker oxidizing metal such as zinc and nickel is attached to the metal complexing agent through a sulfur such as dialkyldithiocarbamates, replacing the weaker oxidizing metal in the stabilizing sulfur-containing metal complexing agent with a stronger oxidizing metal such as ferric and cupric ions, thereby destabilizing the thermoplastic, activating the strong-oxidizing metal complex, and thermally degrading the thermoplastic to a low molecular weight material having enhanced biodegradability.

The thermoplastic polymer product may comprise impact modifiers such as copolymers of butene and ethylene, ethylene and methyl acrylate, styrene and butadiene, and terpolymers of ethylene/propylene/nonconjugated diolefins for enhancing physical properties and for incorporating processing oils, nonmetallic metal complexing agents, non-oxidizing metal complexing agents, and metal complexes.

The thermoplastic polymer product may have a thickness of 0.1 mil to twelve inches, preferably 0.2 to 1000 mils, more preferably from 0.2 to 500 mils, still more preferably from 0.2 to 100 mils, most preferably from 0.3 to 10 mils.

The degraded material can be mixed with other materials to provide a fertilizer for farmlands, fields, golf courses, and landfills, since the degraded polymer biodegrades to carbon dioxide, water, and humus.

Examples of the photodegradable, thermal degradable, and biodegradable products of the present invention are as follows:

EXAMPLE 1

About 120 pounds of 95/5 propylene/ethylene copolymer, 30 pounds of 67/24/8/1 blend of 94/6 butene-/ethylene, high density polyethylene, 12 MI polypropylene, and calcium acetyl acetonate are converted into a 1.4 mil film for use as a diaper liner for disposable diapers. After use, the film can be taken to a sewage sludge facility, combined with other organic waste, and mixed in a 1/1 ratio with 18% sewage sludge, and composted for ten days at 140° to 160° F., so that the oxidizing metals in the sludge are complexed. The digested waste is cured in an aerated windrow for three months. During this period and subsequent additional curing of the digested waste, the polymer degrades to a low molecular weight material with enhanced biodegradability.

EXAMPLE 2

About 120 pounds of copolymer of 96/4 propylene-/ethylene resin, 30 pounds of 50/25/23/1/1 blend of a terpolymer of ethylene/propylene/dicyclopentadiene with 100 parts of naphthenic oil, ethylene/methyl acrylate copolymer, high density polyethylene, sodium salt of zinc ethylenediaminetetracetate, and magnesium stearate are converted into a 1.4 mil film liners for sanitary napkins. After use, the discarded film can be composted with sewage sludge and mixed organic waste for 12 days at about 140° F. to 160° F. The digested waste can be cured for five months in an open pile. During this time, the liner degrades to a low molecular weight material with enhanced biodegradability.

EXAMPLE 3

About 114 pounds of copolymer of 97/3 propylene-/ethylene resin with a melt flow index of 20, 6 pounds of a 50/50 titanium dioxide/polyethylene blend, 30 pounds of 25/50/24.9/0.1 blend of 94/6 butene/ethylene copolymer, terpolymer of ethylene, propylene, and ethylidene norbornylene with 100 phr paraffinic oil, high density polyethylene, and magnesium acetylacetonate are converted into a 1.4 mil film.

The film can be used as a liner for disposable diapers. After use, the discarded film can be immersed for four weeks in a 0.3% basic solution of copper, manganese, and iron solution with pH of 7.1 to 9.5. The plastic is dried for two hours at 125° C. to kill the pathogens and degrade the polymer. The polymer product is mixed with other organic waste and composted in an open aerated pile for four months, where it continues to thermally degrade. The degraded polymer product will have enhanced biodegradability, and can be used in a fertilizer mix.

EXAMPLE 4

About 120 pounds of copolymer of 97/3 propylene-/ethylene resin with a MFI of 20, 30 pounds of 24/50/25/0.5/0.5/0.5 blend of 94/6 butene/ethylene copolymer, terpolymer of ethylene, propylene, and ethylidene norbornylene with 100 phr paraffinic oil, polyethylene, magnesium stearate, calcium acetylacetonate, and sodium octanoate are converted into a 1.8 mil film.

The film can be used as a liner for disposable diapers. After use, the discarded film can be immersed for four weeks in a lime solution of 0.5% copper, manganese, and iron solution with pH over 7. The polymer product is heated for two hours at 125° C. to kill the pathogens and degrade the polymer. The polymer product is mixed with other organic waste and composted in an open aerated pile for four months, where it continues to thermally degrade. The degraded polymer product will have enhanced biodegradability and can be used in a fertilizer mix.

EXAMPLE 5

About 120 pounds of polyethylene with a MFI of 20, 30 pounds of 24/50/25.85/0.05/0.05/0.05 blend of 94/6 butene/ethylene copolymer, terpolymer of ethylene, propylene, and ethylidene norbornylene with 100 phr paraffinic oil, polyethylene, magnesium octanoate, calcium acetylacetonate, and naphthenic acid are converted into 6 mil film.

The film can be used as bags for chemicals and fertilizers. After use, the discarded bags can be immersed for four weeks in a lime solution of 1% copper, manganese, and iron solution with pH over 7. The bags are heated for two hours at 125° C. to kill the pathogens and degrade the polymer. The polymer products are mixed with other organic waste and composted in an open pile for six months, where it continues to thermally degrade. The degraded polymer product will have enhanced biodegradability.

EXAMPLE 6

About 120 pounds of polypropylene with a melt flow index of 12, 30 pounds of 25/35/25/13/1/1 blend of 94/6 butene/ethylene, terpolymer of ethylene, propylene, and ethylidene norbornylene with 50 phr naphthenic oil, high density polyethylene, ethylene/methyl acrylate copolymer, octanoic acid, and magnesium acetylacetonate are fed to a commercial cast extruder and converted into 2 mil film.

The film can be used as a fumigation film. The discarded film can be covered with a lime solution containing 0.4% ferric ammonium citrate, so that oxidizing metals can be complexed by the metal complexing agents. The polymer product is heated for up to two hours at 125° C. to dry the plastic, kill the pathogens, and degrade the polymer. The polymer will continue to thermally degrade in a composting pile. The degraded polymer will have enhanced biodegradability and can be mixed with fertilizer for golf courses and lawns.

Also, the treated and degraded film will exhibit enhanced biodegradability, as shown by higher rates of cumulative carbon dioxide evolution in incubated soil at 27° C. over a period of several months as compared to standard polyethylene film.

EXAMPLE 7

About 120 pounds of polystyrene and 30 pounds of 98/1/1 blend of 45/55 styrene/butadiene copolymer with 100 parts of paraffinic oil, sodium salt of magnesium hydroxyethylethylenediaminetetraacetate, and calcium naphthenate are converted into foamed polystyrene cups.

After use, the discarded paper cups can be immersed for four weeks in a lime solution containing 1% ferric ammonium citrate and manganese citrate. The polymer product was heated for two hours at 125° C. to dry the polymer, kill the pathogens, and degrade the polymer. The polymer will continue to thermally degrade in an open composting pile. The degraded polymer will possess enhanced biodegradability, and can be used in a fertilizer mix.

Also, the degraded cups will exhibit higher rates of cumulative carbon dioxide evolution in incubated soil at 27° C. over a period of several months as compared to standard polyethylene film.

EXAMPLE 8

About 120 pounds of copolymer of 94/6 propylene-/ethylene resin with a melt flow index of 20, 30 pounds of 32/60/4/2/2 blend of 94/6 butene/ethylene, terpolymer of ethylene, propylene, and 1,4-hexadiene, ethylene/acrylic acid copolymer with 6.5% acrylic acid, naphthenic acid, and magnesium octanoate are fed to a commercial cast extruder and made into 1.4 mil film.

The film can be used as liners for disposable diapers and sanitary napkins. After use, the discarded film can be immersed for two days in a lime solution containing 1% ferric ammonium citrate and manganese acetate. The polymer product is then composted with other garden and organic waste for one month in an aerated windrow and for seven months in an open pile to kill pathogens and biodegrade the organic waste. During this period the polymer thermally degrades. The degraded polymer will have enhanced biodegradability and can be used in a fertilizer mix.

EXAMPLE 9

About 120 pounds of copolymer of 97/5 propylene-/ethylene resin with a melt flow index of 20, 30 pounds of 60/31/1/4 blend of 94/6 butene/ethylene, terpolymer of ethylene, propylene, and 1,4-hexadiene, ethylene/acrylic acid copolymer with 6.5% acrylic acid, magnesium acetyl acetonate, and maleated polypropylene made under the tradename of Epolene E-43 are fed to a commercial cast extruder and converted into 1.6 mil film.

The film can be used as liners for disposable diapers and for sanitary napkins. After use, the discarded film can be immersed for four weeks in sewage sludge. The plastic is then heated for two hours at 125° C. to dry the plastic, kill the pathogens, and degrade the polymer. The mixture is combined with other organic waste, and composted in an aerated windrow for 60 days and in open pile for four months. During this period the polymer product continues to thermally degrade. The degraded polymer product has enhanced biodegradability, and can be used in a fertilizer mix.

EXAMPLE 10

About 120 pounds of 96/4 propylene/ethylene resin with a melt flow index of 20, 30 pounds of a 59.5/22/18/0.1/0.4 blend of a ethylene/propylene/ethylidene norbornylene terpolymer containing 50 phr of naphthenic oil, 94/6 butene/ethylene copolymer, ethylene/methyl acrylate copolymer, ferric acetyl acetonate and zinc dimethyldithiocarbamate are fed to a commercial cast extruder and converted into 0.9 mil film.

The film can be used as liners for disposable diapers and sanitary napkins. The discarded liners are taken to a sewage disposal plant where they are shredded, mixed with slightly alkaline sludge and wood chips for 15 minutes. The mixture is placed over a bed of wood chips, and aerated for 28 days at temperatures of about 55° to 65° C. The compost is screened, and cured in an open pile for 180 days. The compost can be used as a cover for landfills, golf courses, and farms. The degraded polymer will have enhanced biodegradability.

EXAMPLE 11

About 112 pounds of polyethylene resin with a melt flow index of 20, 8 pounds of a 50/50 titanium dioxide/-polyethylene blend, 30 pounds of a 50/32/10/4/2/2 of a blend of a ethylene/propylene/ethylidene norbornylene terpolymer containing 100 phr of paraffinic oil, 94/6 butene/ethylene copolymer, ethylene/methyl acrylate copolymer, high molecular weight maleated polypropylene, sodium linoleate, and calcium acetyl acetonate are fed to a commercial cast extruder and converted into 0.8 mil film.

The film can be used as liners for disposable diapers and sanitary napkins. The discarded liners are taken to a sewage disposal plant where they are shredded, mixed with slightly alkaline sludge, and wood chips for 15 minutes. The mixture is placed over a bed of wood chips, and aerated for 30 days temperatures of about 55° to 65° C. The compost is then screened for large pieces and cured in an open pile for 180 days. The compost can be used as a cover for landfills, golf courses, and farms. The degraded polymer will have enhanced biodegradability.

EXAMPLE 12

About 110 pounds of 12 MI polypropylene, 10 pounds of 80/20 polyethylene/furnace black concentrate, and 30 pounds of a blend of 50/26/20/1/3 ethylene/propylene/ethylidene norbornylene terpolymer containing 50 parts of paraffinic oil, high density polyethylene, ethylene/methyl acrylate copolymer, potassium naphthenate, and maleated polypropylene of high molecular weight made by DuPont under the tradename of Bynel 379 are made into film. The bags are kept outside for five days, and then are taken to a sewage treatment facility, where the films are immersed for four weeks in a 0.5% basic solution of manganese, copper, and iron. The films are mixed with sewage sludge and dried for one hour at 130° C. and then composted for 45 days in aerated windrows, and cured for four months in an open pile. The treated, composted and cured films will degrade to a low molecular weight, possessing enhanced biodegradability.

EXAMPLE 13

About 120 pounds of 12 MI polypropylene, 20% of a blend 50/25/24/0.5/0.5 terpolymer of ethylene/-propylene/ethylidene norbornylene with 100 phr paraffinic oil, 94/6 butene/ethylene copolymer, high density polyethylene, calcium acetylacetonate, and magnesium octanate. The films can be used for fertilizer bags and after use be put into a ditch, covered with lime, sprayed with a ferric containing fungicide, and composted with lime, manure and garden waste The film will degrade during the next 18 months to a low molecular weight material which will possess enhanced biodegradability. Alternatively, the bags can be sent to sewage sludge treatment facility, where they can be subjected to the preceding treatments. Lime contains oxidizing metals which can be complexed by metal complexing agents in the polymer product, thereby being incorporated into the polymer product and converting the metal complexing agents into active oxidants.

EXAMPLE 14

About 120 pounds of 12 MI of polypropylene are blended with 20 parts of a blend of 50/25/21.5/3/0.5 of ethylene/propylene/ethylidene norbornylene with 100 phr paraffinic oil, 94/6 butene/ethylene copolymer, high density polyethylene, ethylene/acrylic acid copolymer, and calcium acetyl acetonate. The film can be used to cover sweet corn seeds in New Jersey during March and April. The exposed film will degrade by early July. And the unexposed film can be removed, placed into a ditch, sprayed with a lime solution, and composted with manure and garden waste to convert the metal complexing agent to an active oxidant, and to promote thermal, photo-, and biodegradation The film will degrade in the compost over the next eighteen months with periodic aeration. Film exposed to sunlight will photodegrade more rapidly than untreated film.

In still another aspect of the invention, the grower wraps the film around hay to keep it moist. After using the hay, the grower discards the bag into a ditch, and covers the film with lime, manure and garden waste in order to compost the mixture. The film will degrade thermally at composting temperatures, and become amenable to biodegradation.

EXAMPLE 15

About 120 pounds of polyethylene resin with a melt flow index of 30, 30 pounds of a 25/50/20/4/0.5/0.5 of a blend of ethylene/methyl acrylate copolymer, terpolymer of ethylene, propylene, and dicyclopentadiene containing 100 phr of naphthenic oil, high density polyethylene, ethylene/acrylic acid copolymer with 7.5% acrylic acid, sodium octanoate, and calcium acetylacetonate are fed to a commercial cast extruder and converted into a 1.3 mil film.

The film can be used as liners for disposable diapers and sanitary napkins. The discarded films are mixed with organic waste and taken to a sewage disposal plant where they are shredded and mixed with 18% sewage sludge and wood chips for 15 minutes. The mixture is placed over a bed of wood chips, and aerated for 30 days at temperatures of about 55° to 65° C. The compost is then screened for large pieces and cured in an open pile for 180 days. The compost can be used as a cover for landfills, golf courses, and farms. The degraded plastic in the mixture will possess enhanced biodegradability.

EXAMPLE 16

About 95 pounds of a high viscosity polyamide resin, 5 pounds of a 90/9.6/0.2/0.2 blend of polyamide, ethylene/methyl acrylate copolymer, potassium naphthenate, and calcium acetylacetonate are converted using standard plastic machinery into fibers, and yarn guides.

The fiber and guides are discarded after use, mixed with organic waste, and taken to a sewage disposal plant where they are shredded and mixed with 18% sewage sludge and wood chips for 15 minutes. The mixture is placed over a bed of wood chips, and aerated for 30 days at temperatures of about 55° to 65° C. The compost is then screened for large pieces and cured in an open pile for 180 days. The compost can be used as a cover for landfills, golf courses, and farms. The degraded plastic in the mixture will possess enhanced biodegradability.

EXAMPLE 17

About 99.6 pounds of a polyethylene terephthalate resin and 0.2 each of sodium and calcium acetylacetonate are converted using standard plastic machinery into bottle containers.

The bottles after use can be mixed with organic waste and taken to a sewage disposal plant where they are shredded and mixed with 189% sewage sludge and wood chips for 15 minutes. The mixture is placed over a bed of wood chips, and aerated for 30 days at temperatures of about 55° to 65° C. The compost is then screened for large pieces and cured in an open pile for 180 days. The compost can be used as a cover for landfills, golf courses, and farms. The degraded plastic in the mixture will possess enhanced biodegradability.

EXAMPLE 18

About 110 pounds of polypropylene resin with a melt flow index of 30, 40 pounds of a 50/25/23.9/0.5/0.04/0.56 blend of a ethylene/propylene/1,4-hexadiene terpolymer, ethylene/methyl acrylate copolymer, high density polyethylene of 18 MI, 30 MI polypropylene, potassium octonate, sodium acetylacetonate, and antioxidant tetrakis(methylene( 3,5-di-tert-butyl-4hydroxyhydrocinnamate)}methane and tris( 2,4-di-tert-butylphenyl)phosphite can be converted into one mil film.

The film can be used in January for planting seeds of watermelons in the Imperial Valley of California to increase early yields. The film will start to photodegrade after about 30 to 70 days and will conserve water. Also, the tuck or unexposed layer can be removed and placed in a ditch, sprayed with a lime solution containing 1% ferric ammonium citrate and cupric acetate, and composted with manure and garden waste to convert the metal complexing agent to an active oxidant over a period of 12 months, which will promote thermal, photo- and biodegradation.

EXAMPLE 19

About 740 pounds of polypropylene resin with a melt flow of 12, 180 pounds of a blend of 50/25.2/24.6/1/1/0.5 ethylene/propylene/ethylidene norbornylene terpolymer having a 31 ML 1+8 Mooney Viscosity at 100° C., 3.7% ethylidene norbornylene, and an ethylene content of 56% high density polyethylene of 18 MI, polypropylene of 30 MI, magnesium naphthenate, calcium acetylacetonate, and tetrakis(methylene(3,5-di-tert-butyl-hydroxyhydrocinnamate)}methane and tris(2,4-di-tert-butylphenyl)phosphite and 80 pounds of a blend of polypropylene and 20% of furnace carbon black with an average particle size of about 75 nm. and 2% dimethyl succinate polymer with 4-hydroxy-2,2,6,6-tetramethyl-1-piperidine ethanol and 0.5% of tetrakis(methylene(3,5-di-tert-butyl-hydroxyhydrocinnamate)}methane and tris(2,4-di-tert-butylphenyl)phosphite are converted into 1 mil mulch for use in South Carolina. Surfaces exposed to the sunlight will photodegrade in about 50 to 100 days. The tuck can be removed at the end of the season and placed in a ditch, sprayed with a lime solution containing 1% ferric ammonium citrate and manganese acetate and composted for up to 24 months with manure and garden waste to convert the metal complexing agent to an active oxidant and promote thermal, photo-, and biodegradation. The film will have enhanced biodegradability.

I claim:

1. Process for composing thermoplastic material including the steps of providing thermoplastic material including a thermoplastic polymer and polymeric composting promoting agent selected from the group consisting of metal complexing agents and metal complexes, and mixtures thereof, in a composting effective amount to convert in the presence of oxidizing metal selected from a group consisting of copper, iron, manganese and cobalt, to an active oxidant, contacting said thermoplastic material with a media containing oxidizing metal selected from a group consisting of garden waste, food waste, paper, wood chips, sewage sludge, mixed solid organic waste, sewage sludge and mixed solid organic waste, lime, manure, and liquid media solutions of oxidizing metals, to cause said oxidizing metal to convert said polymeric composting converting agent to said active oxidant in an amount sufficient to cause said active oxidant to thermally degrade said thermoplastic polymer to a low molecular weight material having enhanced biodegradability under composting conditions and concomitantly subjecting said thermoplastic material to composting conditions to at least partially biodegrade said low molecular material.

2. Process according to claim 1 wherein said thermoplastic material is contacted with said media containing said oxidizing metal under composting conditions.

3. Process according to claim 1 wherein said thermoplastic material is contacted with said media containing said oxidizing metal under non-composting conditions.

4. Process according to claim 1 wherein either said metal complexing agent or said metal complexes or both are prooxidants.

5. Process according to claim 1 wherein one of said metal complexing agents is a stabilizer and wherein said step of contacting said thermoplastic material with said media contacting said oxidizing metal is the further step of causing said oxidizing metal to substantially destabilize said stabilizer.

6. Process according to claim 1 wherein said media is sewage sludge and mixed solid organic waste and wherein said contacting step is the step of contacting said thermoplastic material with said sewage sludge and said mixed solid organic waste for about 3 days to about 8 weeks at temperatures of about 15° C. to about 80° C., and where in said subjecting step is the step of subjecting said thermoplastic material to composting conditions selected from a group consisting of aerated windrows compost piles, and conveyor systems for about 1 to about 90 days and curing the mixture of sewage sludge and mixed solid organic waste and thermoplastic material from about 1 day to about 10 months in an open compost pile.

7. Process according to claim 1 wherein said media in a sewage sludge and mixed solid organic waste and wherein said contacting step is the step of contacting said thermoplastic material with said sewage sludge and said mixed solid organic waste for about 5 days to 4 weeks at temperatures of 15° C. to 80° C., and wherein said subjecting step is the step of subjecting said thermoplastic material to composting conditions selected from a group consisting of aerated windrows, compost piles, and conveyor systems for about 5 to about 90 days and curing the mixture of sewage sludge and mixed solid organic waste and thermoplastic material from about 7 days to about 6 months in an open compost pile.

8. Process according to claim 1 wherein said media is sewage sludge and mixed solid organic waste and wherein said contacting step is the step of contacting said thermoplastic material with said sewage sludge and said mixed solid organic waste for about 7 days to 3 weeks at temperatures of about 15° C. to about 80° C., and wherein said subjecting step is the step of subjecting said thermoplastic material to composting conditions selected from a group consisting of aerated windrows, compost piles, and conveyor systems for about 10 to about 60 days and curing the mixture of sewage sludge and mixed solid organic waste and thermoplastic material from about 7 days to about 6 months in an open compost pile.

9. Process according to claim 1 wherein said media is garden waste and wherein said contacting step and said subjecting step are contacting said thermoplastic material with said garden waste for about 1 to about 8 weeks at temperatures of about 15° C. to about 80° C. under composting conditions selected from a group consisting of aerated windrows, compost piles, and conveyor systems, and wherein said process includes the further step of curing the mixture of garden waste and thermoplastic material for about 3 days to about 12 months in an open compost pile.

10. Process according to claim 1 wherein said media is garden waste and wherein the mixture of garden waste and thermoplastic material is sprayed with a 0.1% to 5% basic solutions of manganese, copper, and iron at a rate of about 0.001% to about 3% of metal based on said waste and heated for about 1 week to about 24 months at temperatures of about 15° C. to about 80° C.

11. Process according to claim 1 wherein said media is sewage sludge and mixed solid organic waste, wherein said process includes the further step of mixing said sewage sludge and said solid organic waste and said thermoplastic material with wood chips for about 5 to about 20 minutes to form a mixture thereof, and wherein said subjecting step is the step of placing said mixture over a bed of wood chips and aerating said mixture for about 1 day to about 4 weeks at temperatures of about 10° C. to about 150° C. and wherein said process includes the further step of curing said mixture for about 2 weeks to about 24 months in an open compost pile.

12. Process according to claim 1 wherein said contacting step is the step of contacting said thermoplastic material with solutions of copper, manganese, cobalt and iron having a pH of 4 to 14 and having metal concentrations of 0.1 to 3% for a period of about two hours to about eight weeks and drying the thermoplastic polymer product for one minute to eight weeks at temperatures of 15° C. to 150° C., and wherein said subjecting step is the step of mixing the treated and dried thermoplastic material with sewage sludge, mixed solid organic waste and/or garden waste to form a mixture thereof and composting said mixture in a group consisting of aerated windrows, compost piles, and conveyor system for about five minutes to about eight weeks, and wherein said process includes the further step of curing said mixture in an open compost pile for about five days to about twelve months.

13. Process according to claim 1 wherein the metal complexing agent contains a nonoxidizing metal and comprises materials containing —NH$_2$, —CO—, —COO—, —SH, and —S—S— groups, and wherein said materials are selected from the group consisting of beta-ketones, beta-ketoesters, phosphonic acids, aminocarboxylic acids, polyphosphates, hydroxycarboxylic acid, fatty acids, and polymeric type metal complexing agents including maleated polyolefins, copolymers of ethylene and acrylic acids, copolymers of ethylene and methacrylic acids, and terpolymers of ethylene, propylene, and acrylic acid.

14. Process according to claim 1 wherein said liquid media solutions of oxidizing metals contains about 0.005 to about 5% of oxidizing metal.

15. Process according to claim 14 wherein said liquid media solutions of oxidizing metals has a pH of 6 to 12.

16. Process according to claim 1 wherein said sewage sludge has a solids content of about 2% to about 50%.

17. Process according to claim 16 wherein said solids content of the sewage sludge is about 4% to about 30%.

18. Process according to claim 1 wherein said media is a mixture of sewage sludge and mixed organic solids having a ratio of about 0.1 to about 1.8 of sewage sludge to mixed organic solids.

19. Process according to claim 1 wherein said thermoplastic polymer product is exposed to said oxidizing metal contained in said media for a period of about 5 minutes to about 10 months at temperatures of about 0° C. to about 150° C., and mixed with a waste material for a period of about 1 minute to about 10 months at temperatures of about 0° C. to about 150° C.

* * * * *